US012340874B1

(12) United States Patent
Palaniappan et al.

(10) Patent No.: US 12,340,874 B1
(45) Date of Patent: Jun. 24, 2025

(54) ARTIFICIAL NEURAL NETWORK MODELS FOR PREDICTION OF DE NOVO SEQUENCING OF CHAINS OF AMINO ACIDS

(71) Applicant: Verily Life Sciences LLC, South San Francisco, CA (US)

(72) Inventors: Krishnan Palaniappan, San Francisco, CA (US); Peter Cimermancic, Mountain View, CA (US); Roie Levy, San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 1234 days.

(21) Appl. No.: 16/170,158

(22) Filed: Oct. 25, 2018

Related U.S. Application Data

(60) Provisional application No. 62/581,276, filed on Nov. 3, 2017.

(51) Int. Cl.
| | |
|---|---|
| *G16B 40/00* | (2019.01) |
| *G06N 3/044* | (2023.01) |
| *G06N 3/084* | (2023.01) |
| *G06N 3/088* | (2023.01) |
| *G16B 30/00* | (2019.01) |
| *G16B 40/10* | (2019.01) |

(52) U.S. Cl.
CPC .............. *G16B 40/00* (2019.02); *G06N 3/044* (2023.01); *G06N 3/084* (2013.01); *G06N 3/088* (2013.01); *G16B 30/00* (2019.02); *G16B 40/10* (2019.02)

(58) Field of Classification Search
CPC ........................................................ G16B 40/00
See application file for complete search history.

(56) References Cited

U.S. PATENT DOCUMENTS

| 11,862,298 B1 | 1/2024 | Palaniappan | |
|---|---|---|---|
| 2018/0005676 A1* | 1/2018 | Neil ........................ | G06N 3/08 |
| 2019/0018019 A1* | 1/2019 | Shan ....................... | G06F 17/16 |

OTHER PUBLICATIONS

Luong et al., "Effective Approaches to attention-based neural machine translation," arXiv:1508.04025 v5, (Sep. 2015).*
CN106202068 (Machine translated English version) (2016).*
(Continued)

*Primary Examiner* — Hyun D Park
(74) *Attorney, Agent, or Firm* — Kilpatrick Townsend & Stockton LLP

(57) ABSTRACT

The present invention relates to proteomics, and techniques for predicting de novo sequencing of chains of amino acids, such as peptides, proteins, or combinations thereof. Particularly, aspects of the present invention are directed to a computer implemented method that includes obtaining a digital representation of a mass spectrum, the digital representation including a plurality of container elements, encoding, using an encoder portion of a bidirectional recurrent neural network of long short term memory cells and gated recurrent unit cells, each container element as an encoded vector, decoding, using a decoder portion of the bidirectional recurrent neural network, each of the encoded vectors into a sequence of amino acids; and recording the sequence of amino acids as a multi-dimensional data set of amino acids types and a probability of each of the amino acid types in each position of the complete amino acid sequence.

15 Claims, 6 Drawing Sheets

(56) References Cited

OTHER PUBLICATIONS

"Agilent Spectrum Mill MS Proteomics Workbench", Sherenga de Novo Sequencing, Available online at: http://proteomics.broadinstitute.org/millhtml/sm_instruct/denovo.htm, Feb. 27, 2019, 2 pages.

"Complete & Vendor Neutral Solution for Discovery Proteomics with DDA & DIA", PEAKS Studio, Protein Identification & Quantification Software, PTM & Variant Search, Available online at: http://www.bioinfor.com/peaks-studio/, 2018, 7 pages.

"De Novo Antibody Protein Sequencing with Mass Spectrometry", Rapid Novor Inc, Available online at: https://www.rapidnovor.com/resources/de-novo-protein-sequencing-mass-spectrometry/, Mar. 5, 2019, 6 pages.

"Lutefisk", Lutefisk—de Novo MS/MS Sequencing, Available Online at: http://www.hairyfatguy.com/lutefisk/, Nov. 24, 2008, 4 pages.

"PepNovo", de Novo Sequencing of Low Precision MS/MS Data, CSE Bioinformatics Group, Available online at: http://proteomics.ucsd.edu/Software/PepNovo, Feb. 27, 2019, 2 pages.

"Solutions", Innovative Software Solutions from Digital Proteomics, Feb. 27, 2019, 5 pages.

DiMaggio Jr. et al., "De Novo Peptide Identification via Tandem Mass Spectrometry and Integer Linear Optimization", Analytical Chemistry, vol. 79, No. 4, Feb. 15, 2007, pp. 1433-1446.

Fischer et al., "NovoHMM: A Hidden Markov Model for De Novo Peptide Sequencing", Analytical Chemistry, vol. 77, No. 22, Nov. 15, 2005, pp. 7265-7273.

Griss et al., "Recognizing Millions of Consistently Unidentified Spectra Across Hundreds of Shotgun Proteomics Datasets", Nature Methods, vol. 13, Jun. 27, 2016, 8 pages.

Kim et al., "Spectral Profiles, a Novel Representation of Tandem Mass Spectra and their Applications for De Novo Peptide Sequencing and Identification", Molecular & Cellular Proteomics, vol. 8, No. 6, Jun. 2009, pp. 1391-1400.

Klammer et al., "Modeling peptide fragmentation with dynamic Bayesian networks for peptide identification", Bioinformatics, vol. 24 ISMB 2008, pp. i348-i356.

Ma, "Novor: Real-Time Peptide De Novo Sequencing Software", J. Am. Soc. Mass Spectrom., vol. 26, No. 11, Nov. 2015, pp. 1885-1894.

Ma et al., "Peaks: Powerful Software for Peptide De Novo Sequencing by Tandem Mass Spectrometry", Rapid Communications in Mass Spectrometry, vol. 17, No. 20, Aug. 21, 2003, pp. 2337-2342.

Pevtsov et al., "Performance Evaluation of Existing De Novo Sequencing Algorithms", Journal of Proteome Research, vol. 5, No. 11, Nov. 2006, pp. 3018-3028.

Robotham et al., "UVnovo: A de Novo Sequencing Algorithm Using Single Series of Fragment Ions via Chromophore Tagging and 351 nm Ultraviolet Photodissociation Mass Spectrometry", Anal. Chem., Apr. 5, 2016, 88 (7), pp. 3990-3997.

Tran et al., "De novo peptide sequencing by deep learning", Proceedings of the National Academy of Sciences, vol. 114, No. 31, Aug. 1, 2017, pp. 8247-8252.

Zhang, "De Novo Peptide Sequencing Based on a Divide-and-Conquer Algorithm and Peptide Tandem Spectrum Simulation", Analytical Chemistry, vol. 76, No. 21, Nov. 1, 2004, pp. 6374-6383.

Zhou et al., "A machine learning approach to explore the spectra intensity pattern of peptides using tandem mass spectrometry data", BMC Bioinformatics 2008, 9:325, Jul. 30, 2008, 17 pages.

\* cited by examiner

ARTIFICIAL NEURAL NETWORK MODELS FOR PREDICTION OF DE NOVO SEQUENCING OF CHAINS OF AMINO ACIDS

CROSS-REFERENCE TO RELATED APPLICATION

This application claims the benefit of U.S. Application No. 62/581,276, filed Nov. 3, 2017, titled "Artificial Neural Network Models for Prediction of De Novo Sequencing of Chains of Amino Acids," which is incorporated herein by reference in its entirety.

FIELD OF THE INVENTION

The present invention relates to proteomics, and in particular to techniques (e.g., systems, methods, computer program products storing code or instructions executable by one or more processors) for predicting de novo sequencing of chains of amino acids, such as peptides, proteins, or combinations thereof.

BACKGROUND

Mass spectrometry (MS) is a common method of chemical analysis, whereby the subject chemical species (e.g., a protein, peptide, or small molecule) is ionized and sorted based on mass-to-charge ratio (m/z) of the resultant ions. There are a variety of methods, procedures, and instrumentation (e.g., a mass analyzer) for MS used in proteomics. Typically, the MS procedure begins with ionization of a sample. Techniques for ionization include, for example, electron bombardment, fast atom bombardment, electrospray ionization, and matrix-assisted laser desorption/ionization. Ionization of a sample can result in fragmentation, whereby some of the bonds of the ionized molecules rupture to form smaller, charged fragments. All ions are then separated according to their m/z ratio. This separation typically occurs by applying an electric and/or magnetic field to the ions, causing the ions to predictably accelerate and deflect. Finally, a detector analyzes and determines the abundance of each m/z ratio in a given sample. The detector assesses the abundance by, for example, recording an induced charge or current produced when an ion passes or hits a surface of the mass analyzer. The results of the MS analysis are typically represented in a mass spectrum, which plot intensity against the m/z ratio. The x-axis of the spectrum represents the m/z ratio, and the y-axis represents ion intensity. In some spectra, the intensities can be normalized relative to the highest intensity, such that the y-axis represents relative ion abundance.

MS techniques can be used in proteomics for the analysis and identification of peptides and proteins. A common technique for protein identification by MS is known as protein fingerprinting or bottom-up proteomics. In this technique, a mixture of proteins is first digested into a collection of peptides, which is typically accomplished using an enzyme. The peptides are then subjected to tandem mass spectrometry (MS/MS), where the m/z value of the intact peptide is first recorded (e.g., the precursor ion), then isolated, and then fragmented to create daughter (or fragment) ions. Absolute masses of the resultant ion fragments can be determined from the m/z ratio detected during tandem MS/MS. Peak locations within the experimentally collected MS/MS data provide the mass for each fragment ion, while the height of each peak represents the intensity. Each peak may correspond to a different fragment ion.

There are two primary techniques to determine the amino acid sequence of peptides, proteins, or combinations thereof from the experimentally collected MS/MS data (e.g., the query spectra). In a first technique, known as sequence database searching, a database of peptides and proteins (e.g., Uniprot's human proteome) is used to generate a library of theoretical mass spectra for known peptides and proteins. The masses for the fragment ions are then compared against the library of theoretical mass spectra. The theoretical mass spectra are generally prepared by using computer programs according to methods known in the art. These methods include computer applications that digest a protein in silico to generate a list of theoretical peptide fragments and determine the theoretical masses of the fragments ions. In this way, a computer can be used to predict the theoretical masses of fragment ions that would result from the MS analysis of a given protein. While the theoretical masses can be successfully determined, there are no accurate approaches to predict the intensity of a fragment ion as would be reflected in a mass spectrum, and most MS analysis techniques rely on using a constant for intensities or no intensity information for all fragment ions.

In the second technique, known as spectral library searching, the true observed MS/MS spectra for previously identified peptides or proteins are used to match against the query spectra. However, on average (e.g., 50-75% of the MS/MS features or fragment ions remain unidentified) using common database-based searching strategies. Unidentified query spectra most likely result from low-signal-to-noise events, the absence of the correct peptide sequence in the database (e.g., sequence variants), amino acids containing chemical modifications (e.g., post translational modifications (PTMs)), and/or mixtures of multiple peptide sequences. Collectively, the unidentified peptides greatly limit the characterization of (i) organisms with no or incomplete protein databases, (ii) variable regions in antibodies, (iii) PTMs, and (iv) protein/peptide splicing variants, all of which would improve our understanding of basic biology and disease outcomes. To address these limitations, there is a another technique to determine the amino acid sequence from a query spectra, known as de novo sequencing. In this technique, algorithms attempt to directly infer a peptide sequence from the MS/MS spectrum data, without relying on theoretical sequences and/or spectral libraries. However, current implementations of de novo sequencing are inadequate. Accordingly, the need exists for improved techniques for predicting of mass spectrometry data and de novo sequencing of chains of amino acids, such as peptides, proteins, or combinations thereof.

BRIEF SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method for predicting an amino acid sequence from mass spectrometry data, the method including: obtaining, by a computing device, a digital representation of a mass spectrum, the digital representation including a plurality of container elements, and each container element of the plurality of container elements representing a mass spectra in one or more samples. The method also includes encoding, by the computing device and using an encoder portion of a bidirectional recurrent neural network of long short term memory cells and gated recurrent unit cells, each container element as an encoded vector. The method also includes decoding, by the computing device and using a decoder portion of the bidirectional recurrent neural network, each of the encoded vectors into a sequence of amino acids. The method also includes recording, by the computing device, the sequence of amino acids for each of the encoded vectors as a complete amino acid sequence into a memory, where the complete amino acid sequence is recorded as a multi-dimensional data set of amino acids types and a probability of each of the amino acid types in each position of the complete amino acid sequence. The method also includes utilizing, by the computing device, the multi-dimensional data set of amino acids to identify a known peptide sequence in the one or more samples. Other embodiments of this aspect include corresponding computer systems, apparatus, and computer programs recorded on one or more computer storage devices, each configured to perform the actions of the methods.

Implementations may include one or more of the following features. The method where the container element is a one-hot vector, a set of m/z values and respective abundancies, or a combination thereof that uniquely identifies each ion fragment within the mass spectrum. The method further including appending, by the computing device, a set of metadata features to each container element or the encoded vector for each container element, where the decoding each of the encoded vectors into the sequence of amino acids is performed based on the metadata features. The method where the set of metadata features include at least one of the following: ionization method, mass spectrometer type, fragmentation method, fragmentation energy, peptide charge state, peptide mass-over-charge ratio, and peptide's retention time. The method where the encoded vector is an m-dimensional or one-dimensional vector of m elements, where m corresponds to a number of different m/z values and abundances for the n-most abundant ions. The method further including: comparing, by the computing device, the complete amino acid sequence of the one or more samples to a reference proteome, where the reference proteome is obtained from a database. The method may also include identifying, by the computing device, the known peptide sequence in the one or more samples based on the comparison. Implementations of the described techniques may include hardware, a method or process, or computer software on a computer-accessible medium.

One general aspect includes a non-transitory machine readable storage medium having instructions stored thereon that when executed by one or more processors cause the one or more processors to perform a method including: obtaining a digital representation of a mass spectrum, the digital representation including a plurality of container elements, and each container element of the plurality of container elements representing a mass spectra in one or more samples. The non-transitory machine readable storage medium also includes encoding, using an encoder portion of a bidirectional recurrent neural network of long short term memory cells and gated recurrent unit cells, each container element as an encoded vector. The non-transitory machine readable storage medium also includes decoding, using a decoder portion of the bidirectional recurrent neural network, each of the encoded vectors into a sequence of amino acids. The non-transitory machine readable storage medium also includes recording the sequence of amino acids for each of the encoded vectors as a complete amino acid sequence into a memory, where the complete amino acid sequence is recorded as a multi-dimensional data set of amino acids types and a probability of each of the amino acid types in each position of the complete amino acid sequence. The non-transitory machine readable storage medium also includes utilizing the multi-dimensional data set of amino acids to identify a known peptide sequence in the one or more samples. Other embodiments of this aspect include corresponding computer systems, apparatus, and computer programs recorded on one or more computer storage devices, each configured to perform the actions of the methods.

Implementations may include one or more of the following features. The non-transitory machine readable storage medium where the container element is a one-hot vector, a set of m/z values and respective abundancies, or a combination thereof. The non-transitory machine readable storage medium where the method further includes appending a set of metadata features to each container element or the encoded vector for each container element, where the decoding each of the encoded vectors into the sequence of amino acids is performed based on the metadata features. The non-transitory machine readable storage medium where the set of metadata features include at least one of the following: ionization method, mass spectrometer type, fragmentation method, fragmentation energy, peptide charge state, peptide mass-over-charge ratio, and peptide's retention time. The non-transitory machine readable storage medium where the encoded vector is an m-dimensional or one-dimensional vector of m elements, where m corresponds to a number of different m/z values and abundances for the n-most abundant ions. The non-transitory machine readable storage medium where the method further includes: comparing the complete amino acid sequence of the one or more samples to a reference proteome, where the reference proteome is obtained from a database. The non-transitory machine readable storage medium may also include identifying the known peptide sequence in the one or more samples based on the comparison. Implementations of the described techniques may include hardware, a method or process, or computer software on a computer-accessible medium.

One general aspect includes a system including: one or more processors and non-transitory machine readable storage medium. The system also includes program instructions to obtaining a digital representation of a mass spectrum, the digital representation including a plurality of container elements, and each container element of the plurality of container elements representing a mass spectra in one or more samples. The system also includes program instructions to encode, using an encoder portion of a bidirectional recurrent neural network of long short term memory cells and gated recurrent unit cells, each container element as an encoded vector. The system also includes program instructions to decode, using a decoder portion of the bidirectional recurrent neural network, each of the encoded vectors into a sequence of amino acids. The system also includes program instructions to record the sequence of amino acids for each of the encoded vectors as a complete amino acid sequence into a memory, where the complete amino acid sequence is recorded as a multi-dimensional data set of amino acids types and a probability of each of the amino acid types in each position of the complete amino acid sequence. The system also includes program instructions to utilize the multi-dimensional data set of amino acids to identify a known peptide sequence in the one or more samples. The system also includes where the program instructions are stored on the non-transitory machine readable storage medium for execution by the one or more processors. Other embodiments of this aspect include corresponding computer systems, apparatus, and computer programs recorded on one or more computer storage devices, each configured to perform the actions of the methods.

Implementations may include one or more of the following features. The system where the container element is a one-hot vector, a set of m/z values and respective abundancies, or a combination thereof. The system further including program instructions to append a set of metadata features to each container element or the encoded vector for each container element, where the decoding each of the encoded vectors into the sequence of amino acids is performed based on the metadata features. The system where the set of metadata features include at least one of the following: ionization method, mass spectrometer type, fragmentation method, fragmentation energy, peptide charge state, peptide mass-over-charge ratio, and peptide's retention time. The system where the encoded vector is an m-dimensional or one-dimensional vector of m elements, where m corresponds to a number of different m/z values and abundances for the n-most abundant ions. The system further including: program instructions to compare the complete amino acid sequence of the one or more samples to a reference proteome, where the reference proteome is obtained from a database. The system may also include program instructions to identify the known peptide sequence in the one or more samples based on the comparison. Implementations of the described techniques may include hardware, a method or process, or computer software on a computer-accessible medium.

One general aspect includes a method of training an encoder-decoder network for predicting an amino acid sequence from mass spectrometry data, the method including: obtaining, by a computing device, a plurality of mass spectrometry data sets including peptide sequences. The method also includes pre-processing, by the computing device, the plurality of mass spectrometry data sets to create a first data set and a second data set, where the pre-processing includes (i) identifying spectra data with unknown peptide identities, annotating the spectra data with unknown peptide identities, and adding the spectra data with unknown peptide identities having a predetermined q-value to the first data set; and (ii) identifying spectra data with known peptide identities, annotating the spectra data with known peptide identities, and adding the spectra data with known peptide identities irrespective of their q-value to the second data set. The method also includes inputting, by the computing device, a batch of spectra data from the first data set into the encoder-decoder network in a first training process. The method also includes adjusting, by the computing device, weights and biases of the encoder-decoder network in response to the first training process. The method also includes repeating, by the computing device, the inputting and the adjusting using other batches of spectra data from the first data set until a predetermined number of batches of spectra data from the first data set have been processed. The method also includes inputting, by the computing device, a batch of spectra data from the second data set into the encoder-decoder network in a second training process. The method also includes adjusting, by the computing device, weights and biases of the encoder-decoder network in response to the second training process. The method also includes repeating, by the computing device, the inputting and the adjusting using other batches of spectra data from the first data set until (i) the predetermined number of batches of spectra data from the first data set have been processed, or (ii) all batches of spectra data from the first data set and the second data set are processed. Other embodiments of this aspect include corresponding computer systems, apparatus, and computer programs recorded on one or more computer storage devices, each configured to perform the actions of the methods.

Implementations may include one or more of the following features. The method further including: determining, by the computing device, an error in successive values from the first training process and the second training process after all batches of spectra data from the first data set and the second data set are processed; selecting, by the computing device, a validation batch of spectra data including spectra data from the first data set and the second data set in a 1:1 ratio. The method may also include inputting, by the computing device, the validation batch of spectra data into the encoder-decoder network in a third training process. The method further including: determining, by the computing device, an error in successive values from the first training process and the second training process after all batches of spectra data from the first training data set and the training second data set are processed. The method may also include repeating, by the computing device, the first training process, the second training process, and the third training process with different values for one or more hyperparameters. The method may also include selecting, by the computing device, an optimal set of values of the one or more hyperparameters based on error from evaluation on the first training process, the second training process, and the third training process; selecting, by the computing device, a testing batch of spectra data including spectra data from the first data set and the second data set in a 1:1 ratio. The method may also include inputting, by the computing device, the testing batch of spectra data into the encoder-decoder network in a fourth training process. The method may also include determining, by the computing device, an error on the fourth training process. The method where the one or more hyperparameters include at least one of the following hyperparameters: learning rate, degree of learning rate decay, batch size, number of hidden nodes in a recurrent neural network, number of hidden layers in the recurrent neural network, number of layers in a fully-connected neural network, drop out probability for the recurrent neural network cells, drop out probability for the fully-connected neural network layers, cell types within the recurrent neural network, fully-connected neural network activation function, and the predetermined number of batches of spectra data from the first data set. Implementations of the described techniques may include hardware, a method or process, or computer software on a computer-accessible medium.

As used herein, the terms "various", "some", "certain", etc. embodiments or aspects may be the same embodiments or aspects, different embodiments or aspects, some embodiments or aspects that are the same, or some embodiments or aspects that are not the same.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present invention will be better understood in view of the following non-limiting figures, in which.

DETAILED DESCRIPTION

I. Introduction

Figure 1A:
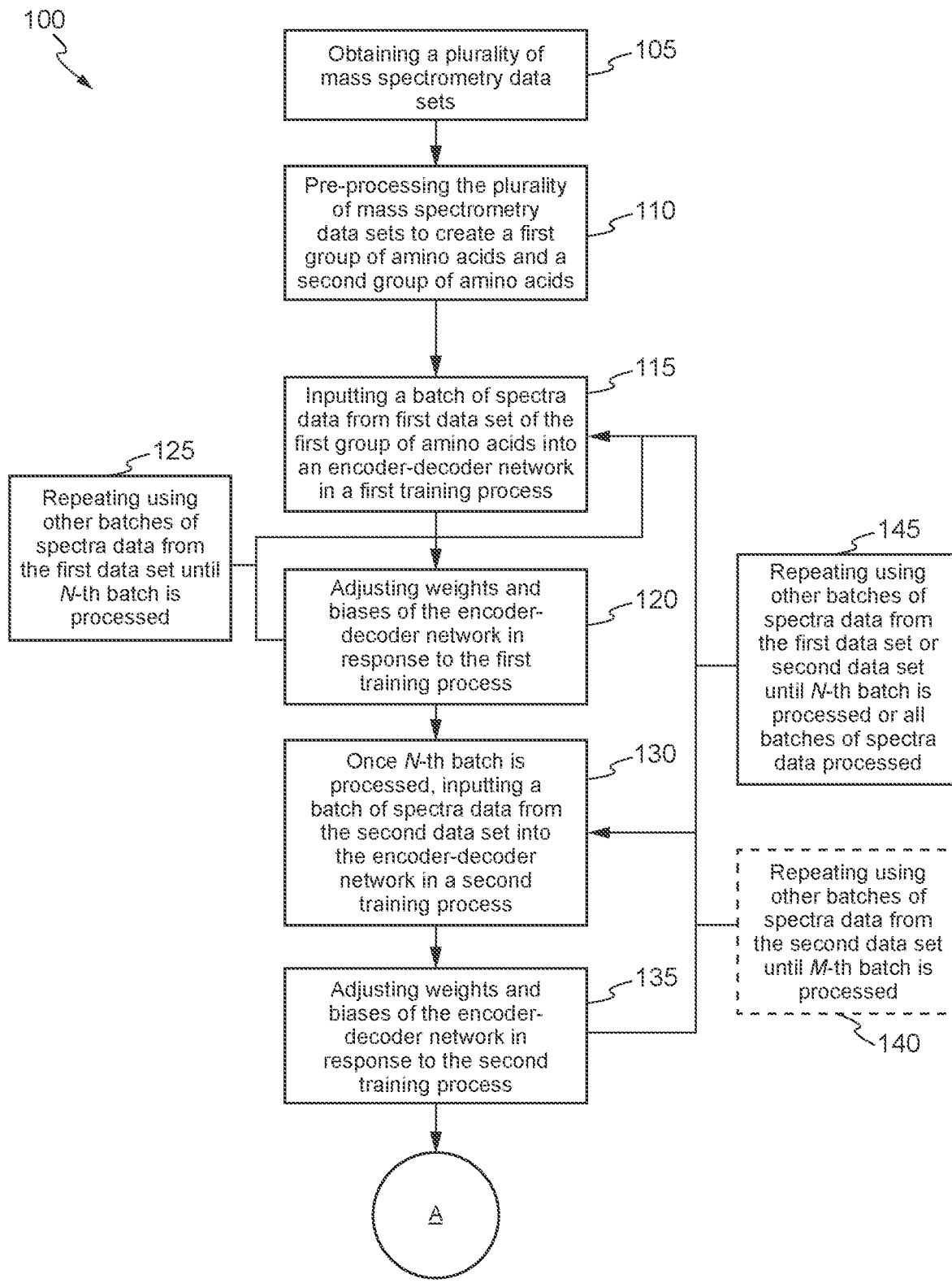
FIGS. 1A and 1B show an exemplary flow for training an encoder-decoder network for predicting an amino acid sequence with a de novo sequencing technique that utilizes a machine learning component in accordance with some aspects of the invention.

In various embodiments, one or more methods are provided for using a machine-learning technique to predict an amino acid sequence from the mass spectrum, without relying on theoretical sequences and/or spectral libraries (i.e., a de novo sequencing technique that utilizes a machine learning component). For example, a prediction can include probabilities of each amino acid at each position within an amino acid sequence such as a peptide or protein. The machine-learning-based prediction results in improved accuracy, coverage, and efficiency of predicting an amino acid sequence from the mass spectrum, which can improve the accuracy, coverage, and efficiency of identifying peptides, proteins, or combinations thereof in a sample.

Conventionally, analysis by a tandem mass spectrometer has been used to identify peptides, proteins, or combinations thereof in a sample. As discussed herein, analysis with the tandem mass spectrometer typically includes two approaches: database searching and de novo sequencing. Database searching includes comparing the query spectra of an unknown peptide or protein to a database of mass spectra data (i.e., theoretical sequences and/or spectral libraries) to find a match with a known peptide sequence, the peptide or protein with the highest matching score will be selected as the peptide or protein for the unknown peptide or protein. This approach fails to recognize novel peptides since it can only match to existing theoretical sequences or previously identified sequences in the database. Alternatively, de novo sequencing is an assignment of fragment ions from a query spectrum to determine an amino acid sequence. In this technique, algorithms attempt to directly infer a peptide sequence from the MS/MS spectrum data, without relying on theoretical sequences and/or spectral libraries. The MS/MS spectrum data can be represented as a histogram of intensity vs. mass (more precisely, m/z) of the ions acquired from the peptide fragmentation inside a mass spectrometer. However, MS/MS spectrum data contains noise, ambiguity, and incomplete data sets, which lends itself to a complicated problem of pattern recognition and global optimization on the noisy, ambiguous, and incomplete data. This problem is typically handled by global dynamic programming, divide and conquer, or integer linear programming. Consequently, an unexperienced application of existing deep learning architectures does not work directly on this problem since neural networks are often known to be good at simulating human brain capability, senses and intuition, rather than such precise optimization tasks.

To address these problems and computational challenges, various embodiments are directed to techniques for developing and implementing a sophisticated deep learning architecture for improving the accuracy of de novo sequencing, thereby improving upon the algorithmic analyses performed to identify peptides and proteins within samples going through mass spectroscopy. For example, one illustrative embodiment of the present disclosure comprises a method for predicting an amino acid sequence from mass spectrometry data. In some aspects, the method comprises obtaining a digital representation of a mass spectrum, the digital representation including a plurality of container elements, and each container element of the plurality of container elements representing a mass spectra; encoding, using an encoder portion of a bidirectional recurrent neural network of long short term memory cells and gated recurrent unit cells, each container element as an encoded vector; decoding, using a decoder portion of the bidirectional recurrent neural network, each of the encoded vectors into a sequence of amino acids; and recording the sequence of amino acids for each of the encoded vectors as a complete amino acid sequence into a memory. The complete amino acid sequence is recorded as a multi-dimensional data set of amino acids types and a probability of each of the amino acid types in each position of the complete amino acid sequence.

Various embodiments, integrate the long short term memory cells and gated recurrent unit cells in the bidirectional recurrent neural network with an optional attention mechanism between the encoder and decoder to learn features of tandem mass spectra, fragment ions, and sequence patterns for predicting peptides or proteins. Consequently, a greater diversity and number of peptides or proteins could be identified in a given MS/MS experiment, including protein/peptide modifications (e.g., post-translational modifications, splice variants, cross-linking, etc.). That is, the protein "vocabulary" dealt with by the techniques described herein is much larger than just the 20+ amino acids dealt with by conventional techniques. In some embodiments, a two-tier training approach may be implemented to expand the protein "vocabulary" and overcome challenges that stem from modified residues (for example, the number of spectra containing a given modification might be too low for effective training). Experimental results show that the various embodiments described herein consistently surpassed conventional global dynamic programming and existing deep learning architectures in de novo peptide sequencing.

Advantageously, these techniques can overcome the computationally intensive and inaccurate problem of de novo sequencing that includes both pattern recognition and global optimization on noisy, ambiguous, and incomplete data, and provide accuracy and efficiency of predicting an amino acid sequence directly from the mass spectrum. The improved prediction of amino acid sequences via a de novo sequencing technique that utilizes a machine learning component in accordance with the various embodiments discussed herein, greatly increases the number of peptides that can be accurately identified directly from the mass spectrum (e.g., current methods only identify up to 45% of first stage of mass spectrometry (MS1) events).

II. Techniques for Prediction of Amino Acid Sequences of Peptides or Proteins

FIGS. 1A, 1, 3, and 4 depict simplified flowcharts depicting processing performed for prediction of an amino acid sequence according to various embodiments. The steps of FIGS. 1A, 1B, 3, and 4 may be implemented in the system environments of FIGS. 2 and 5, for example. As noted herein, the flowcharts of FIGS. 1A, 1B, 3, and 4 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

Figure 1B:
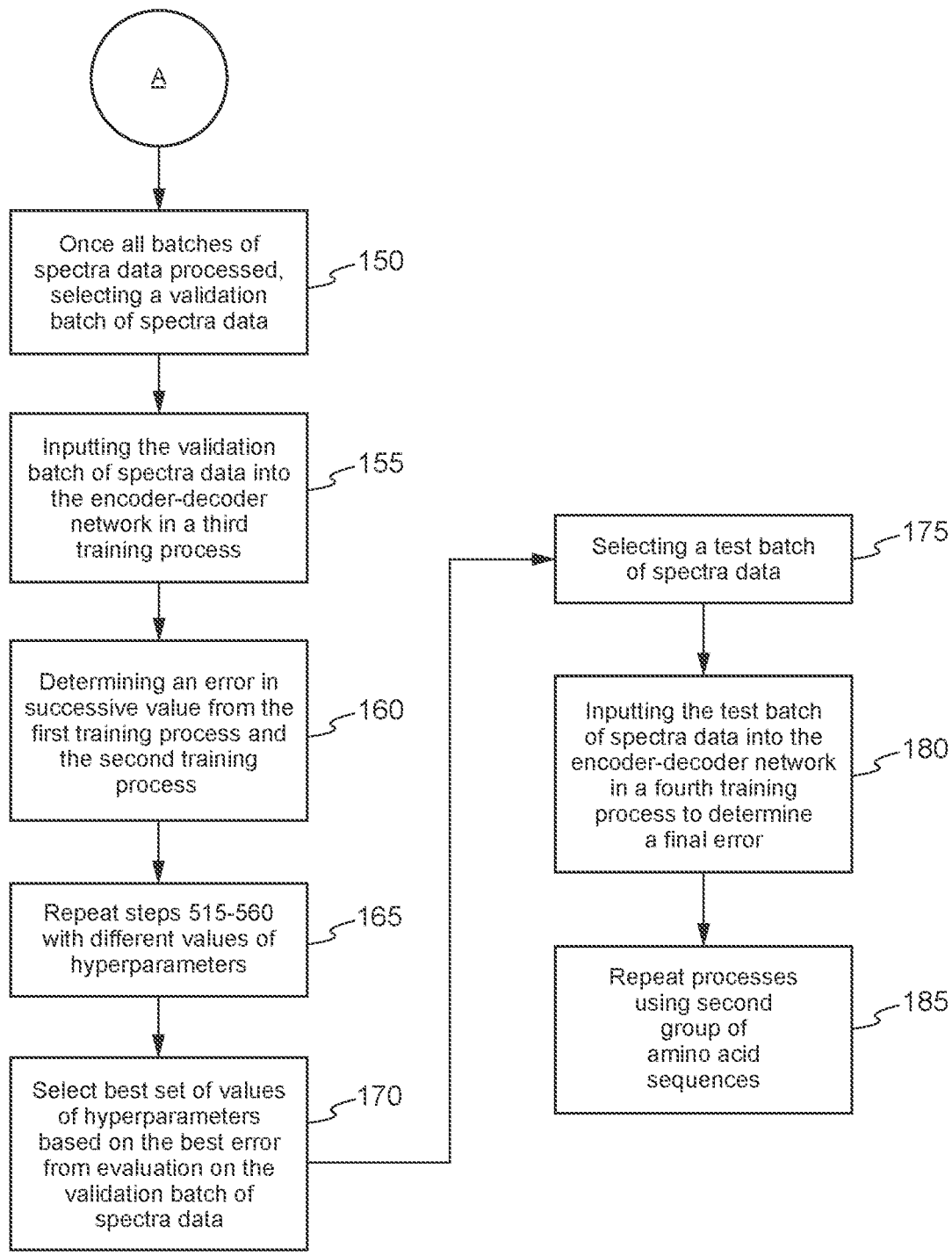

FIGS. 1A and 1B depict a simplified flowchart 100 illustrating a process for training an encoder-decoder network for predicting an amino acid sequence from mass spectrometry data such as from a mass spectrum. With reference to FIG. 1A, at step 105, a plurality of mass spectrometry data sets may be obtained comprising peptide sequences. In some embodiments, the plurality of mass spectrometry data sets are obtained by a computing device from one or more private or public database sources, such as MassIVE Repository, PRIDE, and ProteomeXchange. The private or public database sources may be a centralized, standards compliant, data repository for proteomics data, including protein and peptide identifications, post-translational modifications and supporting spectral evidence. In certain embodiments, the plurality of mass spectrometry data sets may further include peptide or protein sequences, peptide or protein variant sequences (e.g., post-translational modifications), splice variants, isoforms, mutations, and/or enzymatic processing.

At step 110, the plurality of mass spectrometry data sets may be pre-processed to create a first group of amino acid sequences comprising a first data set and a second data set, and a second group of amino acid sequences comprising a third data set and a fourth data set. As used herein, the terms "first", "second", "third" . . . "sixth", etc. identify and distinguish particular data sets, components, or processes and are not used herein to indicate a specific order of use or performance, unless otherwise stated. In various embodiments, the preprocessing includes sorting the spectra data based on types of amino acid residues within the mass spectrometry data sets. For example, twenty-two amino acids are naturally incorporated into peptide chains and are called proteinogenic or natural amino acids. Of these twenty-two amino acids, twenty are encoded by the universal genetic code. The remaining two, selenocysteine and pyrrolysine, are incorporated into proteins by unique synthetic mechanisms. When two or more amino acids combine to form a peptide, the elements of water are removed, and what remains of each amino acid is called an amino acid residue. α-Amino-acid residues are therefore structures that lack a hydrogen atom of the amino group (—NH—CHR—COOH), or the hydroxyl moiety of the carboxyl group ($NH_2$—CHR—CO—), or both (—NH—CHR—COO—); all units of a peptide chain are therefore amino-acid residues. The amino acid residue in a peptide that has an amino group that is free, or at least not acylated by another amino-acid residue (it may, for example, be acylated or formylated), is called the N-terminal; it is at the N-terminus. The amino acid residue that has a free carboxyl group, or at least does not acylate another amino-acid residue (it may, for example, be acylate ammonia to give —NH—CHR—CO—$NH_2$) is called the C-terminal; it is at the C-terminus.

Furthermore, some peptide or protein chains undergo post-translational modification. Post-translational modification refers to the covalent and generally enzymatic modification of proteins during or after protein biosynthesis. Post-translational modifications can occur on the amino acid side chains or at the protein's C- or N-termini. Post-translational modifications can extend the chemical repertoire of the twenty standard amino acids by modifying an existing functional group or introducing a new one such as phosphate. Phosphorylation is a very common mechanism for regulating the activity of enzymes and is one of the most common post-translational modifications. One challenge with using machine learning for chemically modified residues is that the number of spectra containing that modification might be too low for effective training; but this can be addressed by a two-tiered training approach that includes first training the encoder-decoder network on the standard amino acid residues, and then extending its capabilities to other modifications by fine-tuning the original encoder-decoder network. Consequently, in various embodiments, the preprocessing includes sorting the mass spectrometry data sets into a first group of amino acid sequences having standard amino acid residues and a second group of amino acid sequences having other modifications such as post-translational modifications.

In various embodiments, the preprocessing may further include sorting each of the first group of amino acid sequences and the second group of amino acid sequences based on accuracy of the protein or peptide identifications within the mass spectrometry data sets. False Discovery Rate (FDR) and Q-value may be used to assess and score the accuracy of the plurality of mass spectrometry data sets. As described herein, the FDR for a set of proteins or peptides may be the expected percent of false predictions in the set of predictions. To describe the confidence of a specific protein or peptide identification, a Q-value may be defined as the minimal FDR required to accept the identification, after having considered all possible thresholds. In some embodiments, the pre-processing is performed by the computing device and comprises: (i) identifying spectra data in each of the first group of amino acid sequences and the second group of amino acid sequences with unknown peptide identities, annotating the spectra data with unknown peptide identities, and adding the spectra data with unknown peptide identities having a predetermined Q-value, for example, a Q-value of less than 0.0001, to the first data set or third data set, respectively (e.g., "easy" cases); and (ii) identifying spectra data each of the first group of amino acid sequences and the second group of amino acid sequences with known peptide identities, annotating of the spectra data with known peptide identities, and adding the spectra data with known peptide identities irrespective of their Q-value to the second data set or the fourth data set, respectively (e.g., "difficult" cases). In certain embodiments, the annotating the spectra data can be performed using known software techniques, such as using MaxQuant.

In certain embodiments, the identifying spectra data with unknown peptide identities includes using a spectral matching approach. For example, a spectral matching approach may include: (i) identifying spectra data with amino acid residues, annotating the spectra data with unknown peptide identities, and adding the spectra data with unknown peptide identities having a predetermined Q-value, for example, a Q-value of less than 0.0001, to the first data set (e.g., "easy" cases); and (ii) identifying spectra data with known peptide identities, annotating of the spectra data with known peptide identities, and adding the spectra data with known peptide identities irrespective of their Q-value to the second data set (e.g., "difficult" cases). In certain embodiments, the identifying spectra data with unknown peptide identities includes using a spectral matching approach. For example, a spectral matching approach may include: (i) selecting a list of peptides that are expected to be identified as well as a decoy set with peptide sequences reversed, (ii) generating a theoretical MS2 spectra for true and decoy peptides, (iii) pairwise matching of all theoretical vs measured MS2 spectra, (iv) calculating a score for each comparison, and (v) fitting statistical models to scores for true and decoy peptides to calculate FDR and Q-values. In contrast to this approach for identifying spectra data with unknown peptide identities (where MS datasets are used and assumptions are made on the identity of peptides in the sample but the identity of the peptides are not known for sure), identifying spectra data with known peptide identities may include using MS datasets where the identity of the peptides going into the MS are precisely known. For example, identifying spectra data with known peptide identities may include chemically synthesizing one peptide at a time (this is in contrast to identifying spectra data with unknown peptide identities where the peptide mixture is obtained from a cell culture or tissue lysate), and inputting each peptide into the MS.

Thereafter, the first data set, the second data set, the third data set, and the fourth data set are utilized for training, validation, and testing the encoder-decoder network. Conventional training techniques build models that are generalizable and that may train on the first, second, and third set, and test using the fourth set, and then repeat for all combinations. However, this type of training may suffer from inaccuracy since it is too general. The first data set, the second data set, the third data set, and the fourth data set may be divided into three subsets each, for training, validation, and testing, respectively. To overcome this problem, in various embodiments, the first data set, the second data set, the third data set, and the fourth data set are portioned into subsets for training, validation, and testing. For example, the first data set may include a first training data set, a first validation data set, and a first testing data set, while the second data set includes a second training data set, a second validation data set, and a second testing data set, the third data set includes a third training data set, a third validation data set, and a third testing data set, and the fourth data set includes a fourth training data set, a fourth validation data set, and a fourth testing data. This approach have increase the probability of batch effects, but the batch effects usually come from the computing device. In certain embodiments, the model is fine-tuned specific to the computing device, to minimize the probability of the batch effects, and thus the overall accuracy of the training model is higher than a generalized model.

At step 115, a batch of spectra data from the first training data set may be input into an encoder-decoder network in a first training process. In some embodiments, the inputting is performed by the computing device and the encoder-decoder network comprises a bidirectional recurrent neural network of multiple layers of long short term memory (LSTM) cells and gated recurrent unit (GRU) cells as the encoder and decoders portions of the network. The encoder-decoder network is a sequence to sequence mapping model. In particular, an RNN encoder-decoder network takes a sequence as input and generates another sequence as output.

For example, a batch of spectra data can be considered as a variable-length source sequence which can be input and a sequence of amino acids identified from the batch of spectra data is generated as an output which again is a sequence. The encoder-decoder network comprises of two parts: an encoder and a decoder. The encoder network is that part of the network that takes the input sequence and maps it to an encoded representation of the sequence. The encoded representation is then used by the decoder network to generate an output sequence.

A recurrent neural network (RNN) is a network with loops in it, allowing information to persist. Long Short Term Memory networks are a special kind of RNN, capable of learning long-term and short-term dependencies (e.g., the gap between where relevant information was discovered in the network and the point where the relevant information is needed in the network to predict the next object). As used herein, a "long short term memory cell" is a unit of a recurrent neural network comprising multiple interacting layers that can keep a piece of information for long or short periods of time during work and protect the gradient inside the cell from detrimental changes during the training. For example, a LSTM cell may comprise three gates (input, forget, output), and a cell unit. The gates may be configured to use a sigmoid activation, while input and cell state may be transformed with the hyperbolic tangent, or tanh function. As used herein, a "gradient recurrent unit cell" is a unit of a recurrent neural network that modulates the flow of information inside the unit, however, without having a separate memory cell. The activation of the GRU cell at time t is a linear interpolation between the previous activation and the candidate activation where an update gate decides how much the unit updates its activation, or content. This procedure of taking a linear sum between the existing state and the newly computed state is similar to the LSTM cell. The GRU cell, however, does not have any mechanism to control the degree to which its state is exposed, but exposes the whole state each time.

In various embodiments, the encoder network maps a variable-length source sequence such as a batch of spectra data from the first training data to a fixed-dimensional vector representation, and the decoder network maps the vector representation back to a variable-length target sequence such as an amino acid sequence. For categorical variables that may be present in the batch of spectra data where no ordinal relationship exists, integer encoding may not be enough for the algorithms to process the spectra data. As such, some embodiments include encoding the spectra data as a one-hot vector. For example, a one-hot encoding may be applied to the integer representation, which removes the integer encoded variable and adds a new binary variable for each unique integer value. A single input instance (corresponding to a single set of spectra data) is thus defined as an array of m/z values and their abundances for the n-most abundant ions. In certain embodiments, the variable-length target sequences are represented as a multi-dimensional data set of amino acids types (e.g., twenty proteinogenic or natural amino acids) and probability of each amino acid type in each position of the sequence, for example, position in a peptide as columns and amino acid types as rows.

Figure 2:
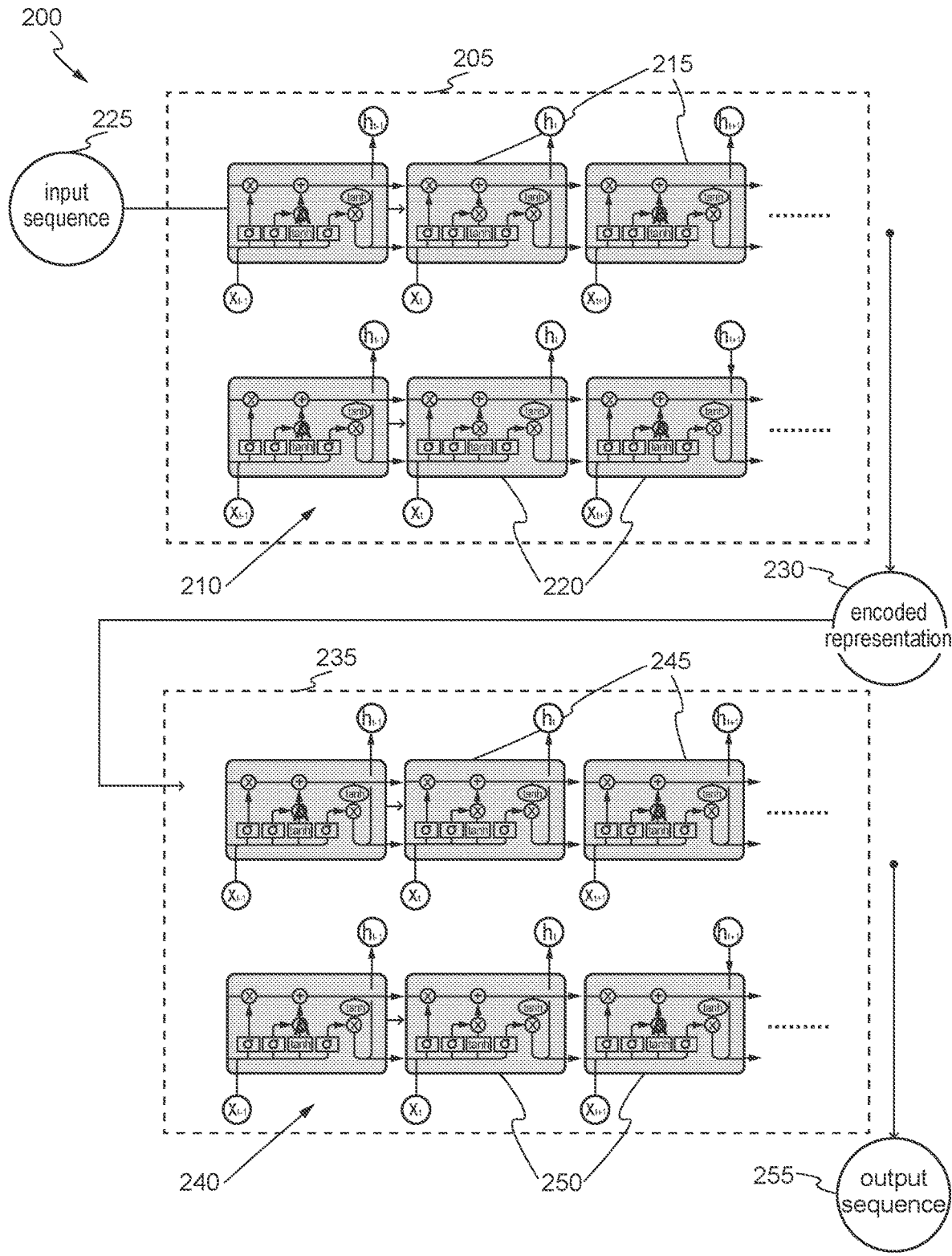
FIG. 2 shows a block diagram of an encoder-decoder network in accordance with some aspects of the invention.

As shown in FIG. 2, the encoder-decoder network 200 may comprise an encoder portion 205 including a bidirectional recurrent neural network 210 of LSTM cells 215 and GRU cells 220. In some embodiments, the encoder portion 205 takes an input sequence 225 (a variable-length source sequence), which in step 115 is a batch of spectra data from the first training data set, and maps the input sequence 225 to an encoded representation 230 (fixed-dimensional vector representation) of the sequence. In certain embodiments, the encoded representation 230 of the input sequence 225 may be a n-dimensional vector of the batch of spectra data from the first training data set. The encoder portion 205 is configured such that each training sequence can be provided forwards and backwards to two separate recurrent neural networks (RNNs), outputs of which are concatenated and then connected to the same output layer. Unlike conventional RNNs, bidirectional RNNs utilize both the previous and future context, by processing the data from two directions with two separate hidden layers. One layer processes the input sequence in the forward direction, while the other processes the input in the reverse direction. The output of a current time step is then generated by concatenating a vector from each hidden layer. Accordingly, for every point in a given sequence, the encoder portion 205 has complete, sequential information about all points before and after it, and is capable of reading the input sequence 225, one time step at a time, to obtain the encoded representation 230. Also, because the encoder portion 205 is free to use as much or as little of this context as necessary, there is no need to find a (task-dependent) time-window or target delay size.

The encoder-decoder network 200 may further comprise a decoder portion 235 including a bidirectional recurrent neural network 240 of LSTM cells 245 and GRU cells 250. The decoder portion 235 is configured such that the encoded representation 230 obtained, for example, from each training sequence can be passed through the decoder portion 235 to obtain a variable-length target sequence of amino acids 255. In some embodiments, the decoder portion 235 takes the encoded representation 230, which in step 115 is a n-dimensional vector of the batch of spectra data from the first training data set, and maps the encoded representation 230 back to a variable-length target sequence of amino acids 255. In certain embodiments, the variable-length target sequence of amino acids 255 is provided as a multi-dimensional data set of amino acids types (e.g., twenty proteinogenic or natural amino acids) and probability of each amino acid type in each position of the sequence.

While the encoder-decoder network 200 has been described at some length and with some particularity with respect to an encoder portion 205 including a bidirectional recurrent neural network 210 and a decoder portion 235 including a bidirectional recurrent neural network 240, it is not intended that the encoder-decoder network 200 be limited to only two neural networks operating in conjunction. Instead, it should be understood the encoder-decoder network 200 described herein is an exemplary embodiment, and that the encoder-decoder network 200 is to be construed with the broadest sense to include variations of the specific design and/or performance need described herein, as well as other variations that are well known to those of skill in the art. In some embodiments, the encoder-decoder network 200 is an ensemble of neural networks that includes at least two neural networks combined to create a learning paradigm or model to solve the problem of predicting an amino acid sequence from mass spectrometry data. For example, significant improvement in performance has been seen when multiple (up to 50) neural networks are trained with the encoder-decoder architecture described herein. In certain embodiments, the ensemble is implemented using a specific number and/or type of neural networks from a possible pool or group of neural networks. The results from training each of the neural networks (i.e., the component predictions) may then be combined using plurality voting or majority voting for classification tasks, and averaging or weighted averaging for regression tasks.

In some embodiments, the first training process may include: (i) for each input (X), performing a feed-forward pass on each intermediary layer (e.g., LSTM cells, hidden layers, fully connected layers, etc.) of the encoder-decoder network 200 to compute the outputs of each layer, then at the output layers to obtain a final output (X'); (ii) measuring a deviation between the final output (X') and the input targets (X), e.g., using a loss function such as squared root or mean-squared error, and calculating an error value for one or more nodes, cells, neurons, or layers within the encoder-decoder network; (iii) back propagating each error value back through the encoder-decoder network staring from the final output (X') until each node, cell, neuron, or layer has an associated error value which roughly represents its contribution to the final output (X'); and (iv) calculating a gradient of the loss function using the associated error values.

With reference back to FIG. 1A, at step 120, weights and biases of the encoder-decoder network may be adjusted in response to the first training process. In some embodiments, adjusting the weights and biases includes feeding the gradient of the loss function calculated in step 115 into an optimization process, which updates or adjusts the weights and biases for the one or more nodes, cells, neurons, or layers in an attempt to minimize the loss function. Accordingly, as the encoder-decoder network is trained, the nodes, cells, or neurons in the intermediate layers organize themselves in such a way that the different nodes, cells, or neurons learn to recognize different characteristics of the total input space. After training, when an arbitrary input pattern is present which contains noise or is incomplete, the nodes, cells, or neurons in the hidden layers of the network will respond with an active output if the new input contains a pattern that resembles a feature that the individual nodes, cells, or neurons have learned to recognize during their training. Optionally, the first training process may further include a pre-training process to determine initial weights and biases for the one or more nodes, cells, neurons, or layers that approximate the final solution to avoid potential problems with the backpropagation of the error values. In certain embodiments, the encoder portion and the decoder portion share weights and biases, use different sets of weights and biases, or include a combination of similar and different weights and biases.

At step 125, the inputting and the adjusting in steps 115 and 120 are repeated using other batches of spectra data from the first training data set until a predetermined number of batches of spectra data from the first training data set have been processed. In some embodiments, a discrepancy between the first data set (e.g., "easy" cases) and the second data set (e.g., "difficult" cases) is created such that the encoder-decoder network does not learn to predict only the first data set (e.g., "easy" cases). For example, a training strategy may be used in which every N-th batch or after a predetermined number of batches of spectra data from the first training data set have been processed, one or more batches of spectra data from the second training data set are used to train the encoder-decoder network. The N-th batch or the predetermined number may be a hyperparameter to be optimized in later processes.

At step 130, a batch of spectra data from the second training data set may be input into the encoder-decoder network in a second training process. In some embodiments, the second training process is similar to the first training processes, as discussed with respect to step 115. At step 135, weights and biases of the encoder-decoder network may be adjusted in response to the second training process. In some embodiments, the adjustment of the weights and biases is performed in a similar manner to the optimization process discussed with respect to step 120. Optionally, at step 140, the inputting and the adjusting in steps 130 and 135 are repeated using other batches of spectra data from the second training data set until a predetermined number of batches of spectra data from the second training data set have been processed. For example, a training strategy may be used in which every M-th batch or after a predetermined number of batches of spectra data from the second training data set have been processed, one or more batches of spectra data from the first training data set may be used again to train the encoder-decoder network. The M-th batch or the predetermined number may be a hyperparameter to be optimized in later processes.

At step 145, the inputting and the adjusting in steps (115 and 120) or (130 and 135) are repeated using other batches of spectra data from the first training data set or the second training set until (i) the predetermined number of batches of spectra data from the first training data set have been processed, or (ii) all batches of spectra data from the first training data set and the second training data set are processed, or optionally, (iii) the predetermined number of batches of spectra data from the second training data set have been processed. In some embodiments, the number of batches of spectra data may be greater than the number of data points in the sets divided by the batch size, and thus all the data points may be reused multiple times (e.g., train the model for 10-20 epochs).

With reference to FIG. 1B, at step 150, a validation batch of spectra is selected comprising spectra from the first validation data set and the second validation data set in a predetermined ratio. In some embodiments, the predetermined ratio is between 10:1 and 1:1 or between 10:1 and 5:1, for example 1:1. The preposition "between," when used to define a range of values (e.g., between x and y) means that the range includes the end points (e.g., x and y) of the given range and the values between the end points. At step 155, the selected validation batch of spectra may be input into the encoder-decoder network in a third training process. In some embodiments, the third training process is similar to the first training processes, as discussed with respect to step 115. At step 160, an error in successive value from the first training process and the second training process may be determined after all batches of spectra data from the first training data set and the second training data set are processed on the selected validation batch of spectra.

At step 165, steps 115-160 are repeated with different values for hyperparameters of the encoder-decoder network. In some embodiments, the hyperparameters include learning rate, degree of learning rate decay, batch size, number of nodes in the RNNs, number of hidden layers in the RNNs, number of layers in the fully-connected neural network, drop out probability for RNN cells, drop out probability for the fully-connected neural network layers, cell types within the RNNs, fully-connected neural network activation function, the N-th batch or the predetermined number of batches of spectra data from the first training data set, and/or optionally the M-th batch or the predetermined number of batches of spectra data from the second training data set. At step 170, the best set of values of hyperparameters is selected based on the best loss value from evaluation on the first and second validation data sets (e.g., the mean-squared error may be used as a loss function here). At step 175, a testing batch of spectra is selected comprising spectra from the first testing data set and the second testing data set in a predetermined ratio. In some embodiments, the predetermined ratio is between 1:10 and 1:1 or between 1:5 and 1:10, for example 1:1. At step 180, the selected testing batch of spectra may be input into the encoder-decoder network in a fourth training process to determine an error of the encoder-decoder network. At step 185, the afore-mentioned processes may be repeated using the second group of amino acid sequences comprising the third data set and the fourth data set, to ultimately determine the final error of the encoder-decoder network.

Figure 3:
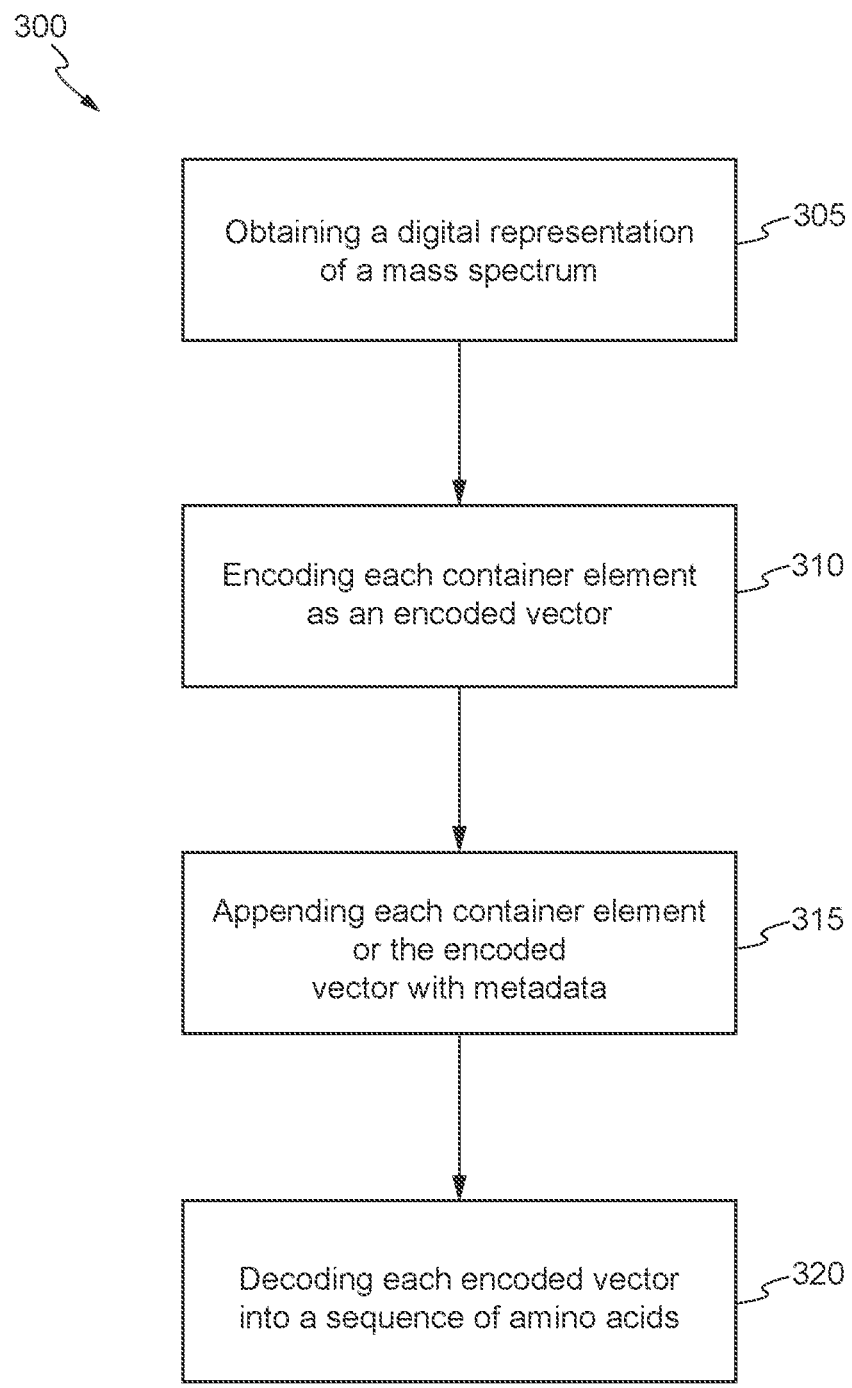
FIG. 3 shows an exemplary flow for predicting an amino acid sequence with a de novo sequencing technique that utilizes a machine learning component in accordance with some aspects of the invention.

FIG. 3 depicts a simplified flowchart 300 illustrating a process for predicting an amino acid sequence from a mass spectrum. At step 305, a digital representation of a mass spectrum may be obtained. In some embodiments, the digital representation includes a plurality of container elements, and each container element of the plurality of container elements represent a mass spectra. The container element refers to an object that stores other objects (its elements) such as a one-hot vector, a set of m/z values and their respective abundancies, or a combination thereof that uniquely identifies each ion fragment within the mass spectra. The mass spectra may be experimental and obtained by a mass spectrometry technique such as tandem MS/MS.

At step 310, each container element may be encoded as an encoded vector. In some embodiments, each container element is encoded, by a computing device, as an encoded vector, which is an m-dimensional or one-dimensional vector of m elements, where m corresponds to the number of different m/z values and their abundances for the n-most abundant ions. The encoding may be performed by an encoder including a bidirectional recurrent neural network of LSTM cells and GRU cells as described with respect to the encoder-decoder network 200 in FIG. 2.

At step 315, each container element or the encoded vector for each container element residue may be appended with metadata. In some embodiments, the metadata includes one or more features of the mass spectra and/or mass spectrometry techniques that could be used to predict the amino acid sequence. In certain embodiments, the one or more features are not part of the mass spectra (what) but nevertheless defines the mass spectra (how, why, where, when, origin, etc). For example, it is known that peptides of different charge or processed with different mass spec machines can result in a different spectrum. Adding such metadata features (e.g., spectral analysis configuration and sample profile) may enhance the prediction of the amino acid sequence from mass spectrometry data. In certain embodiments, adding metadata improves the prediction by at least 20%. In some embodiments, the metadata is appended, by a computing device, to a data structure for either each container element or the encoded vector for each container element. In certain embodiments, the one or more features include: ionization method, mass spectrometer type (e.g., represented as a one-hot vector), fragmentation method (e.g., represented as an one-hot vector), fragmentation energy, peptide charge state (e.g., represented as a 0-1 scaled discrete value), peptide mass-over-charge ratio (e.g., represented as a 0-1 scaled continuous value), and/or peptide's retention time (e.g., represented as a 0-1 scaled discrete value). These metadata values may be scaled to the same scale as the encoded vector concatenated to the metadata values.

At step 320, each encoded vector for each mass spectrum is decoded into a sequence of amino acids based on the set of metadata features. In some embodiments, the encoded vector is decoded, by a computing device, into the sequence of amino acids (e.g., a multi-dimensional vector) that represents a corresponding mass spectra. Thereafter, the amino acid sequences for each of the encoded vectors may be combined into a complete amino acid sequence for a peptide or protein sequence. The complete amino acid sequence is thus the combination of (sub)spectra for sequences of amino acids from all ion fragments of a given peptide or protein sequence. The decoding may be performed by a decoder including a bidirectional recurrent neural network of LSTM cells and GRU cells as described with respect to the encoder-decoder network 200 in FIG. 2. In certain embodiments, the amino acids sequences are recorded into a memory (e.g., non-transitory machine-readable storage medium) such that the amino acids sequences can be used in subsequent processes such as part of database used to identify actual peptides or proteins within the sample introduced to the mass spectrometer. The amino acid sequences (e.g., the complete amino acid sequence) may be represented as a multi-dimensional data set of amino acids types (e.g., twenty proteinogenic or natural amino acids) and a probability of each of the amino acid types in each position of the amino acid sequence, for example, position in a peptide as columns and amino acid types as rows.

The encoder-decoder architecture, as described, is capable of achieving improved results in predicting an amino acid sequence from a mass spectrum. Nevertheless, the encoder-decoder architecture may have a constraint that all input sequences are forced to be encoded to a fixed length encoded vector and lose (at least to some degree) a spatial/temporal resolution for the alignment of the input and output sequences. This is may limit the performance of the encoder-decoder architecture, especially when considering long input sequences, such as very long peptide or protein chains. To overcome this potential constraint, in some embodiments, one or more attention mechanisms are implemented to allow the decoder to "attend" to different parts of the source at each step of the output generation. Attention is the idea of freeing the encoder-decoder architecture from the fixed-length internal representation. This is achieved by keeping the intermediate outputs from the encoder LSTM from each step of the input sequence and training the model(s) to learn to pay selective attention to these inputs and relate them to items in the output sequence. Put another way, each item in the output sequence is conditional on selective items in the input sequence. In some embodiments, an attention model is a method that takes n arguments y1 . . . yn, and a context c. The attention model returns a vector z which may be the summary of the yi, focusing on information linked to the context c. More precisely, the attention model returns a weighted arithmetic mean of the yi, and the weights are chosen according the relevance of each yi given the context c. For example, the context c may be the beginning of the generated amino acid sequence, the yi may be the representations of portions of digital representation of a mass spectrum, and the output may be a representation of the filtered digital representation of a mass spectrum, with a filter placing the focus on the interesting part in the digital representation of a mass spectrum for the amino acid currently generated.

Moreover, in the encoder-decoder architecture, it is assumed that the best output sequence always start with the amino acid having the highest probability, which may not be a valid assumption. For example, a better sequence may have been a sequence that starts with the amino acid that had the second highest probability. To overcome this potentially invalid assumption, in some embodiments, a beam search mechanisms is implemented that allows the encoder-decoder architecture to take the top n amino acids as the input of the decoder sequence, rather than simply considering the highest probable amino acid at the first time step of the decoder as the input of the output sequence. A beam search is a restricted, or modified, version of either a breadth-first search or a best-first search. Beam search is restricted in the sense that the amount of memory available for storing the set of alternative search nodes is limited, and in the sense that non-promising nodes can be pruned at any step in the search. The pruning of non-promising nodes is determined by problem-specific heuristics. The set of most promising, or best alternative, search nodes is called the "beam." Where n is called the beam size which is itself a parameter. Thereafter to compute the second amino acid, each of the top n amino acids are fed into the decoder to obtain all the sequences of length 2, and out of all the sequences of length 2, the top n amino acid sequences of length 2 are chosen for further processing. The third amino acid may then be predicted for the sequence conditioned on the top n amino acid sequences of length 2, and again all the amino acid sequences of length 3 are obtained, and out of all the amino acid sequences of length 3, the top n amino acid sequences of length 3 are chosen for further processing. The process continues until the end. In the end, the top n decoded sequences are provided as output.

Figure 4:
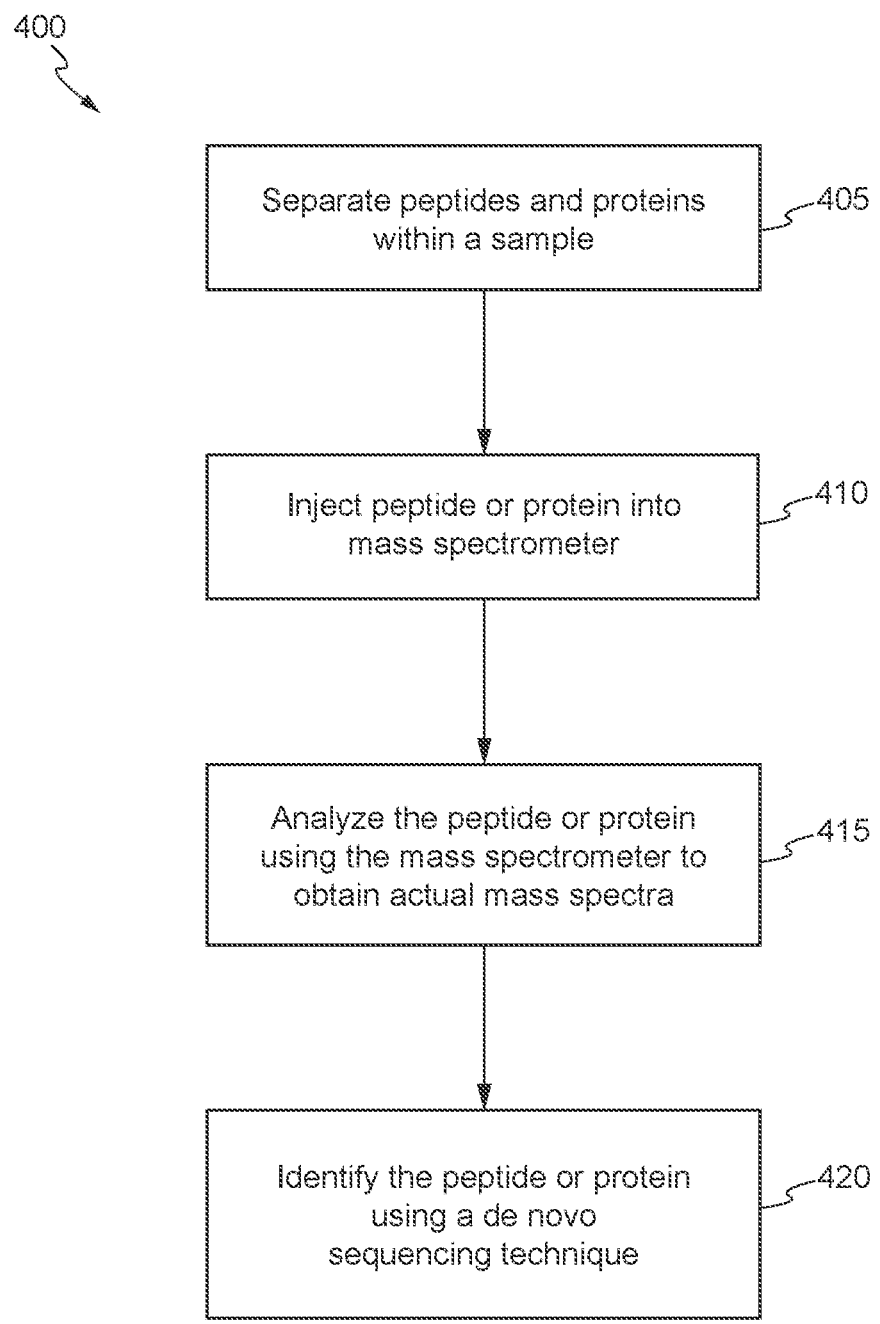
FIG. 4 shows an exemplary flow for identifying a protein or peptide in a sample in accordance with some aspects of the invention.

FIG. 4 depicts a simplified flowchart 400 illustrating a process for using a mass spectrum obtained in accordance with aspects of the present invention to identify actual peptides or proteins within a sample. At step 405, one or more samples (e.g., a biological sample) are obtained, and proteins or peptides are separated. In some embodiments, the one or more samples include a complex mixture of proteins and molecules, which co-exist in a biological medium. The complex mixture of proteins and molecules may be separated using one or more fraction techniques. For example, the techniques of one- and two-dimensional gel electrophoresis and high performance liquid chromatography may be used for the separation of proteins or peptides. In the first technique, gel electrophoresis, the first-dimension is isoelectric focusing (IEF). In this dimension, proteins are separated by their isoelectric point (pI). The second-dimension is SDS-polyacrylamide gel electrophoresis (SDS-PAGE). In this dimension, the proteins are separated according to its molecular weight. Once the proteins are separated, in-gel digestion may occur using one or more enzymes to obtain peptides. In the second technique, high performance liquid chromatography is used to separate peptides after enzymatic digestion of the proteins. A peptide mixture that results from digestion of a protein mixture is separated by one or two dimensions of liquid chromatography.

At step 410, one or more peptides or proteins from the separated peptides or proteins is injected into a mass spectrometer and turned into an ionized form (e.g., fragmented ions) in the gas phase. In some embodiments, the one or more peptides or proteins are ionized in the gas phase using electrospray ionization (ESI) or matrix-assisted laser desorption/ionization (MALDI). In ESI, the ions are created from proteins in solution, and ESI allows fragile molecules to be ionized intact, sometimes preserving non-covalent interactions. In MALDI, the proteins are embedded within a matrix normally in a solid form, and ions are created by pulses of laser light. At step 415, the ionized form of the one or more peptides or proteins in the gas phase are accelerated in an electric or magnetic field for analysis. In various embodiments, steps 410 and/or 415 are performed using MS techniques and systems such as time-of-flight (TOF) MS, fourier transform ion cyclotron resonance (FT-ICR), or tandem mass spectrometry (MS/MS) to obtain mass spectra comprising a two-dimensional data set of mass and intensity values for each fragment ion. The masses and intensities of the resultant fragment ions of the protein or peptides in the sample can be determined from the m/z ratio and abundance detected during MS, respectively.

At step 420, the one or more peptides or proteins from the one or more samples are identified based on a de novo sequencing technique that utilizes a machine learning component as discussed with respect to FIG. 3. In various embodiments, the multi-dimensional data set of amino acids types and probability of each amino acid type in each position of the sequence obtained for each mass spectra may be combined into a sequence of amino acids representing one or more peptides or proteins from the sample. This output can be treated as a Hidden Markov Model (HMM) sequence profile, and used to further improve identification by searching against a reference proteome in a database (e.g., UniProt), even when the prediction of the sequence of amino acids is not perfectly accurate. A proteome is a set of proteins thought to be expressed by an organism. The majority of proteomes are based on the translation of a completely sequenced genome, and will normally include sequences that derive from extra-chromosomal elements such as plasmids or organellar genomes in organisms where these occur.

In some embodiments, the searching against the reference proteome comprises comparing (e.g., using the computing device) the complete amino acid sequence of the one or more samples to a reference proteome, and identifying a peptide sequence in the one or more samples based on the comparison. In certain embodiments, the comparing and the identifying include comparing (e.g., using the computing device) the complete amino acid sequence of the sample to a reference proteome, matching a peptide sequence within the amino acid sequence to a corresponding peptide sequence within the reference proteome, obtaining the identifier of the corresponding peptide sequence from the reference proteome, and applying the identifier to the peptide sequence within the amino acid sequence to identify the peptide sequence within the one or more samples. In other embodiments, the comparing and the identifying include comparing (e.g., using the computing device) the complete amino acid sequence of the sample to a reference proteome, matching one or more portions of the complete amino acid sequence (or one or more portions of a peptide sequence within the amino acid sequence) to one or more corresponding portions of a known peptide sequence, determining a probability that the match between one or more portions of the complete amino acid sequence (or one or more portions of a peptide sequence within the amino acid sequence) and one or more corresponding portions of a known peptide sequence is indicative of the presence of the peptide sequence in the one or more sample, and when the probability is greater than a predetermined threshold (e.g., greater than a 50%, 60%, or 70% probability), obtaining the identifier of the corresponding peptide or protein sequence from the reference proteome, and applying the identifier to the peptide sequence within the amino acid sequence to identify the peptide sequence within the one or more samples. Accordingly, the comparing may not be configured to identify exact matches but instead configured to identify probable matches based on one or more portions of the complete amino acid sequence (or one or more portions of a peptide sequence within the amino acid sequence) and one or more corresponding portions of a known peptide sequence, which may advantageously compensate for variations and modifications in the complete sequence and/or the known peptide sequences.

III. System Environment

Figure 5:
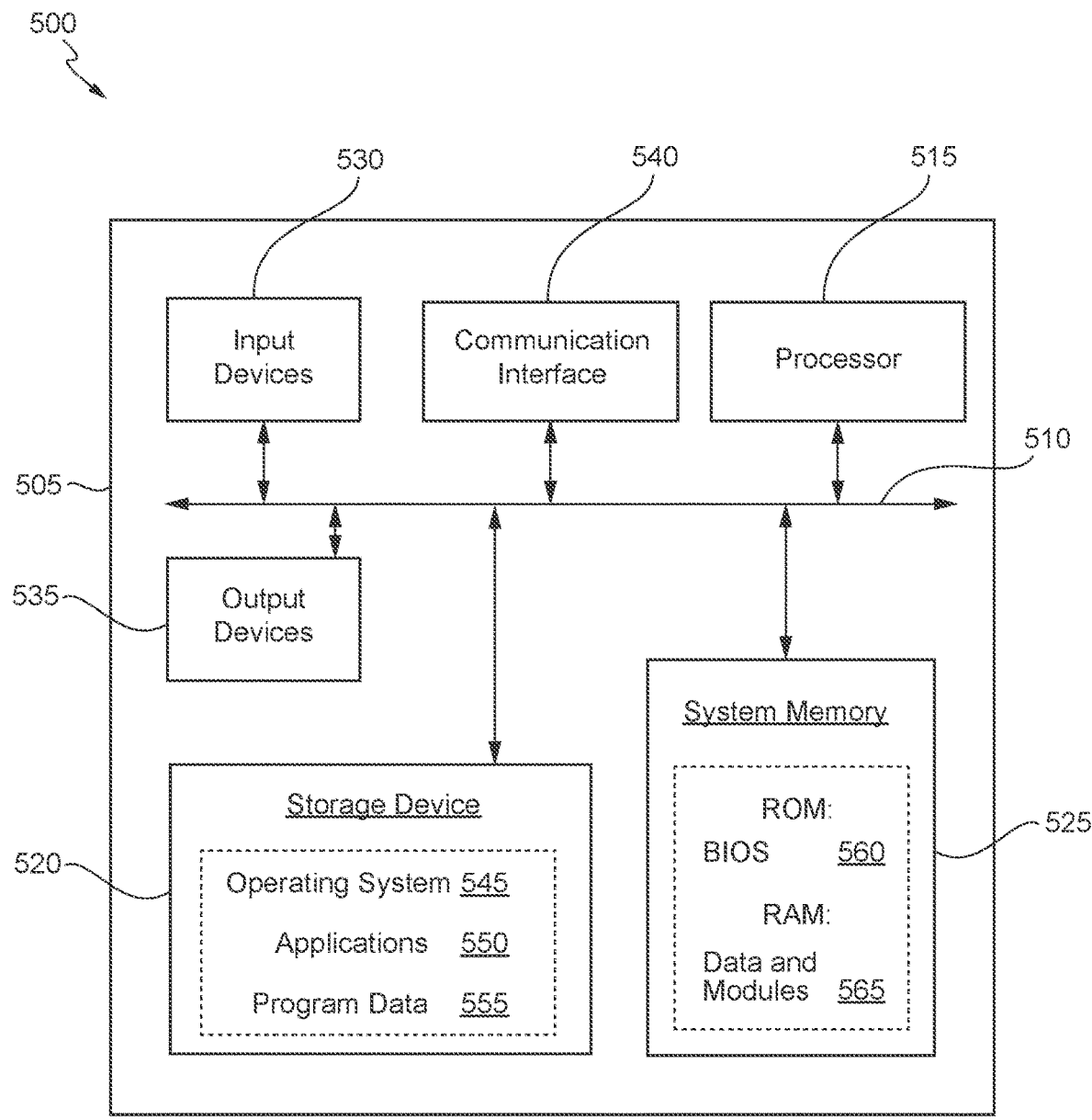
FIG. 5 shows an illustrative architecture of a computing system implemented in accordance with some aspects of the invention.

FIG. 5 is an illustrative architecture of a computing system 500 implemented as some embodiments of the present invention. The computing system 500 is only one example of a suitable computing system and is not intended to suggest any limitation as to the scope of use or functionality of the present invention. Also, computing system 500 should not be interpreted as having any dependency or requirement relating to any one or combination of components illustrated in computing system 500.

As shown in FIG. 5, computing system 500 includes a computing device 505. The computing device 905 can be resident on a network infrastructure such as within a cloud environment, or may be a separate independent computing device (e.g., a computing device of a service provider). The computing device 505 may include a bus 510, processor 515, a storage device 520, a system memory (hardware device) 525, one or more input devices 530, one or more output devices 535, and a communication interface 540.

The bus 510 permits communication among the components of computing device 505. For example, bus 510 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 505.

The processor 515 may be one or more conventional processors, microprocessors, or specialized dedicated processors that include processing circuitry operative to interpret and execute computer readable program instructions, such as program instructions for controlling the operation and performance of one or more of the various other components of computing device 505 for implementing the functionality, steps, and/or performance of the present invention. In certain embodiments, processor 515 interprets and executes the processes, steps, functions, and/or operations of the present invention, which may be operatively implemented by the computer readable program instructions. For example, processor 515 can retrieve, e.g., import and/or otherwise obtain or generate mass spectra, encode each mass spectra, append a set of metadata features to each mass spectra or an encoded vector for each mass spectra, and decode each encoded vector. In embodiments, the information obtained or generated by the processor 515, e.g., the peptide sequence, the mass spectra, the plurality of amino acid residues, the encoded vectors, the decoded vectors, etc., can be stored in the storage device 920.

The storage device 520 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of computing device 505 in accordance with the different aspects of the present invention. In embodiments, storage device 520 may store operating system 545, application programs 550, and program data 555 in accordance with aspects of the present invention.

The system memory 525 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system 560 (BIOS) including the basic routines that help to transfer information between the various other components of computing device 505, such as during start-up, may be stored in the ROM. Additionally, data and/or program modules 565, such as at least a portion of operating system 945, program modules, application programs 550, and/or program data 555, that are accessible to and/or presently being operated on by processor 515, may be contained in the RAM. In embodiments, the program modules 565 and/or application programs 550 can comprise, for example, a processing tool to identify and annotate spectra data, a metadata tool to append data structures with metadata, one or more encoder-decoder networks to predict amino acid sequences, and a comparison tool to compare the complete amino acid sequence of the one or more samples to a reference proteome to identify a peptide sequence in the one or more samples, which provides the instructions for execution of processor 515.

The one or more input devices 530 may include one or more mechanisms that permit an operator to input information to computing device 505, such as, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The one or more output devices 535 may include one or more mechanisms that output information to an operator, such as, but not limited to, audio speakers, headphones, audio line-outs, visual displays, antennas, infrared ports, tactile feedback, printers, or combinations thereof.

The communication interface 540 may include any transceiver-like mechanism (e.g., a network interface, a network adapter, a modem, or combinations thereof) that enables computing device 505 to communicate with remote devices or systems, such as a mobile device or other computing devices such as, for example, a server in a networked environment, e.g., cloud environment. For example, computing device 505 may be connected to remote devices or systems via one or more local area networks (LAN) and/or one or more wide area networks (WAN) using communication interface 540.

As discussed herein, computing system 500 may be configured to train an encoder-decoder network to predict an amino acid sequence from mass spectrometry data, predict the amino acid sequence from mass spectrometry data, and compare the complete amino acid sequence of the one or more samples to a reference proteome to identify a peptide sequence in the one or more samples. In particular, computing device 505 may perform tasks (e.g., process, steps, methods and/or functionality) in response to processor 515 executing program instructions contained in non-transitory machine readable storage medium, such as system memory 525. The program instructions may be read into system memory 525 from another computer readable medium (e.g., non-transitory machine readable storage medium), such as data storage device 520, or from another device via the communication interface 540 or server within or outside of a cloud environment. In embodiments, an operator may interact with computing device 505 via the one or more input devices 530 and/or the one or more output devices 535 to facilitate performance of the tasks and/or realize the end results of such tasks in accordance with aspects of the present invention. In additional or alternative embodiments, hardwired circuitry may be used in place of or in combination with the program instructions to implement the tasks, e.g., steps, methods and/or functionality, consistent with the different aspects of the present invention. Thus, the steps, methods and/or functionality disclosed herein can be implemented in any combination of hardware circuitry and software.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A method for identifying an unknown peptide or protein in a sample, the method comprising:
   obtaining the sample comprising a mixture of proteins and molecules;
   preprocessing the mixture of proteins and molecules to isolate the unknown peptide or protein from the mixture of proteins and molecules;
   analyzing, using a mass spectrometer, the isolated peptide or protein to obtain a mass spectrum comprising a two-dimensional data set of mass and intensity values for each fragment ion from the isolated peptide or protein, wherein the analyzing comprises determining the mass and intensity values for each fragment ion from a m/z ratio and abundance detected by the mass spectrometer;
   generating, by a computing device, a digital representation of the mass spectrum, the digital representation including a plurality of container elements, and each container element of the plurality of container elements is an object that stores other objects including a one-hot vector, a set of m/z values and respective abundancies, or a combination thereof that uniquely identifies each ion fragment within the mass spectrum;
   inputting, by the computing device, the digital representation of the mass spectrum into an encoder-decoder network comprising an encoder portion and a decoder portion, wherein:
      the encoder portion comprises a first bidirectional recurrent neural network of a first set of long short term memory cells and gated recurrent unit cells that are trained to map a variable-length source sequence defined by each container element to a fixed-dimensional vector representation,
      the first bidirectional recurrent neural network is configured to process the variable-length source sequence from start to end and then process the variable-length source sequence from end to start,
      the decoder portion comprises a second bidirectional recurrent neural network of a second set of long short term memory cells and gated recurrent unit cells that are trained to map the fixed-dimensional vector representation back to a variable-length amino acid sequence,
      the second bidirectional recurrent neural network is configured to process the fixed-dimensional vector representation from start to end and then process the fixed-dimensional vector representation from end to start, and the encoder-decoder network is initially trained on a first set of training data comprising standard amino acid residues, and then fine-tuned on a second set of training data comprising post-translational modifications of peptide or protein chains;

encoding, by the computing device and using the encoder portion, each container element as the fixed-dimensional vector representation, which is an m-dimensional or one-dimensional vector of m elements, wherein m corresponds to a number of different m/z values and abundances for n-most abundant ions;

appending, by the computing device, a set of metadata features to each container element or the fixed-dimensional vector representation for each container element, wherein the set of metadata features include: ionization method, mass spectrometer type, fragmentation method, fragmentation energy, peptide charge state, peptide mass-over-charge ratio, peptide's retention time, or a combination thereof;

generating, by the computing device using an attention model, a context vector for each of the fixed-dimensional vector representations based on intermediate outputs from the encoder portion from each step of encoding each of the fixed-dimensional vector representations, wherein the context vector is a weighted arithmetic mean of argument values, and weights are chosen according to relevance of each argument value given a context;

decoding, by the computing device and using the decoder portion, each of the fixed-dimensional vector representation into a variable-length amino acid sequence based on the set of metadata features and the context vector, wherein the variable-length amino acid sequence is represented as a multi-dimensional data set of amino acids types and probability of each amino acid type in each position of a sequence; and identifying, by the computing device and based on the variable-length amino acid sequence, the unknown peptide or protein in order to characterize aspects including a complete sequence, structure, and possible function of the unknown peptide or protein, wherein the identifying comprises:
combining the variable-length amino acid sequences into a complete sequence of amino acids representing the unknown peptide or protein,
comparing the complete sequence of amino acids to a reference proteome, and
identifying a known peptide or protein based on the comparison.

2. The method of claim 1, further comprising:
injecting the isolated peptide or protein into the mass spectrometer;
ionizing the injected peptide or protein in a gas phase using electrospray ionization (ESI) or matrix-assisted laser desorption/ionization (MALDI); and
accelerating the ionized peptides or proteins in the gas phase are accelerated in an electric or magnetic field for analysis,
wherein the preprocessing comprises using gel electrophoresis and/or liquid chromatography to isolate the unknown peptide or protein from the mixture of proteins and molecules, and wherein the fixed-dimensional vector representation is an m-dimensional or one-dimensional vector of m elements, where m corresponds to a number of different m/z values and abundances for the n-most abundant ions, and wherein the decoding comprises mapping the m-dimensional or one-dimensional vector of m elements back to the sequence of amino acids while taking into consideration a set of metadata features and a context vector.

3. The method of claim 1, wherein the identifying further comprises:
matching one or more portions of the complete sequence of amino acids to one or more corresponding portions of a known peptide sequence;
determining a probability that the match between the one or more portions of the complete sequence of amino acids and the one or more corresponding portions of the known peptide sequence is indicative of a presence of the known peptide sequence in the sample; and
when the probability is greater than a predetermined threshold, obtaining an identifier of the corresponding peptide or protein sequence from the reference proteome,
wherein the unknown peptide or protein is identified based on the identifier.

4. The method of claim 1, wherein each long short term memory cell comprises three gates and a cell unit, wherein each of the three gates is configured to use a sigmoid activation, and wherein a cell state is determined by transforming data associated with at least one gate using a hyperbolic tangent function.

5. The method of claim 1, wherein each of the first and the second bidirectional recurrent neural network comprises at least two sets of hidden layers, wherein each set of the hidden layers is configured to processing data in a different direction.

6. A non-transitory machine readable storage medium having instructions stored thereon that when executed by one or more processors cause the one or more processors to perform a method comprising:
obtaining a sample comprising a mixture of proteins and molecules;
preprocessing the mixture of proteins and molecules to isolate an unknown peptide or protein from the mixture of proteins and molecules;
analyzing, using a mass spectrometer, the isolated peptide or protein to obtain a mass spectrum comprising a two-dimensional data set of mass and intensity values for each fragment ion from the isolated peptide or protein, wherein the analyzing comprises determining the mass and intensity values for each fragment ion from a m/z ratio and abundance detected by the mass spectrometer;
generating a digital representation of the mass spectrum, the digital representation including a plurality of container elements, wherein each container element of the plurality of container elements is an object that stores other objects including a one-hot vector, a set of m/z values and respective abundances, or a combination thereof that uniquely identifies each ion fragment within the mass spectrum;
inputting the digital representation of the mass spectrum into an encoder-decoder network comprising an encoder portion and a decoder portion, wherein:
the encoder portion comprises a first bidirectional recurrent neural network of a first set of long short term memory cells and gated recurrent unit cells that are trained to map a variable-length source sequence defined by each container element to a fixed-dimensional vector representation, the first bidirectional recurrent neural network is configured to process the variable-length source sequence from start to end and then process the variable-length source sequence from end to start, the decoder portion comprises a second bidirectional recurrent neural network of a second set of long short term memory cells and gated recurrent unit cells that are trained to map the fixed-dimensional vector representation back to a variable-length amino acid sequence, the second bidirectional recurrent neural network is configured to process the fixed-dimensional vector representation from start to end and then process the fixed-dimensional vector representation from end to start, and the encoder-decoder network is initially trained on a first set of training data comprising standard amino acid residues, and then fine-tuned on a second set of training data comprising post-translational modifications of peptide or protein chains;

encoding, using the encoder portion, each container element as the fixed-dimensional vector representation, which is an m-dimensional or one-dimensional vector of m elements, wherein m corresponds to a number of different m/z values and abundances for n-most abundant ions;

appending a set of metadata features to each container element or the fixed-dimensional vector representation for each container element, wherein the set of metadata features include: ionization method, mass spectrometer type, fragmentation method, fragmentation energy, peptide charge state, peptide mass-over-charge ratio, peptide's retention time, or a combination thereof;

generating, using an attention model, a context vector for each of the fixed-dimensional vector representations based on intermediate outputs from the encoder portion from each step of encoding each of the fixed-dimensional vector representations, wherein the context vector is a weighted arithmetic mean of argument values, and weights are chosen according to relevance of each argument value given a context;

decoding, using the decoder portion, each of the fixed-dimensional vector representation into a variable-length amino acid sequence based on the set of metadata features and the context vector, wherein the variable-length amino acid sequence is represented as a multi-dimensional data set of amino acids types and probability of each amino acid type in each position of a sequence; and identifying, based on the variable-length amino acid sequence, the unknown peptide or protein in order to characterize aspects including a complete sequence, structure, and possible function of the unknown peptide or protein, wherein the identifying comprises:
combining the variable-length amino acid sequences into a complete sequence of amino acids representing the unknown peptide or protein,
comparing the complete sequence of amino acids to a reference proteome, and
identifying a known peptide or protein based on the comparison.

7. The non-transitory machine readable storage medium of claim 6, wherein the preprocessing comprises using gel electrophoresis and/or liquid chromatography to isolate the unknown peptide or protein from the mixture of proteins and molecules, and wherein the fixed-dimensional vector representation is an m-dimensional or one-dimensional vector of m elements, where m corresponds to a number of different m/z values and abundances for the n-most abundant ions, and wherein the decoding comprises mapping the m-dimensional or one-dimensional vector of m elements back to the sequence of amino acids while taking into consideration a set of metadata features and a context vector.

8. The non-transitory machine readable storage medium of claim 6, wherein the identifying further comprises:
matching one or more portions of the complete sequence of amino acids to one or more corresponding portions of a known peptide sequence;
determining a probability that the match between the one or more portions of the complete sequence of amino acids and the one or more corresponding portions of the known peptide sequence is indicative of a presence of the known peptide sequence in the sample; and
when the probability is greater than a predetermined threshold, obtaining an identifier of the corresponding peptide or protein sequence from the reference proteome,
wherein the unknown peptide or protein is identified based on the identifier.

9. The non-transitory machine readable storage medium of claim 6, wherein each long short term memory cell comprises three gates and a cell unit, wherein each of the three gates is configured to use a sigmoid activation, and wherein a cell state is determined by transforming data associated with at least one gate using a hyperbolic tangent function.

10. The non-transitory machine readable storage medium of claim 6, wherein each of the first and the second bidirectional recurrent neural network comprises at least two sets of hidden layers, wherein each set of the hidden layers is configured to processing data in a different direction.

11. A system comprising:
one or more processors; and
a non-transitory machine readable storage medium containing instructions which, when executed on the one or more data processors, cause the one or more data processors to perform actions including:
instructing to obtain a sample comprising a mixture of proteins and molecules;
instructing to preprocess the mixture of proteins and molecules to isolate an unknown peptide or protein from the mixture of proteins and molecules;
instructing to analyze, using a mass spectrometer, the isolated peptide or protein to obtain a mass spectrum comprising a two-dimensional data set of mass and intensity values for each fragment ion from the isolated peptide or protein, wherein the analyzing comprises determining the mass and intensity values for each fragment ion from a m/z ratio and abundance detected by the mass spectrometer;
generating a digital representation of the mass spectrum, the digital representation including a plurality of container elements, and each container element of the plurality of container elements is an object that stores other objects including a one-hot vector, a set of m/z values and respective abundancies, or a combination thereof that uniquely identifies each ion fragment within the mass spectrum;
inputting the digital representation of the mass spectrum into an encoder-decoder network comprising an encoder portion and a decoder portion, wherein:
the encoder portion comprises a first bidirectional recurrent neural network of a first set of long short term memory cells and gated recurrent unit cells that are trained to map a variable-length source sequence defined by each container element to a fixed-dimensional vector representation, the first bidirectional recurrent neural network is configured to process the variable-length source sequence from start to end and then process the variable-length source sequence from end to start, the decoder portion comprises a second bidirectional recurrent neural network of a second set of long short term memory cells and gated recurrent unit cells that are trained to map the fixed-dimensional vector representation back to a variable-length amino acid sequence, the second bidirectional recurrent neural network is configured to process the fixed-dimensional vector representation from start to end and then process the fixed-dimensional vector representation from end to start, and the encoder-decoder network is initially trained on a first set of training data comprising standard amino acid residues, and then fine-tuned on a second set of training data comprising post-translational modifications of peptide or protein chains;

encoding, using the encoder portion, each container element as the fixed-dimensional vector representation, which is an m-dimensional or one-dimensional vector of m elements, wherein m corresponds to a number of different m/z values and abundances for n-most abundant ions;

appending a set of metadata features to each container element or the fixed-dimensional vector representation for each container element, wherein the set of metadata features include: ionization method, mass spectrometer type, fragmentation method, fragmentation energy, peptide charge state, peptide mass-over-charge ratio, peptide's retention time, or a combination thereof;

generating, using an attention model, a context vector for each of the fixed-dimensional vector representations based on intermediate outputs from the encoder portion from each step of encoding each of the fixed-dimensional vector representations, wherein the context vector is a weighted arithmetic mean of argument values, and weights are chosen according to relevance of each argument value given a context;

decoding, using the decoder portion, each of the fixed-dimensional vector representation into a variable-length amino acid sequence based on the set of metadata features and the context vector, wherein the variable-length amino acid sequence is represented as a multi-dimensional data set of amino acids types and probability of each amino acid type in each position of a sequence; and identifying, based on the variable-length amino acid sequence, the unknown peptide or protein in order to characterize aspects including a complete sequence, structure, and possible function of the unknown peptide or protein, wherein the identifying comprises:

combining the variable-length amino acid sequences into a complete sequence of amino acids representing the unknown peptide or protein, comparing the complete sequence of amino acids to a reference proteome, and identifying a known peptide or protein based on the comparison.

12. The system of claim 11, wherein the preprocessing comprises using gel electrophoresis and/or liquid chromatography to isolate the unknown peptide or protein from the mixture of proteins and molecules, and wherein the fixed-dimensional vector representation is an m-dimensional or one-dimensional vector of m elements, where m corresponds to a number of different m/z values and abundances for the n-most abundant ions, and wherein the decoding comprises mapping the m-dimensional or one-dimensional vector of m elements back to the sequence of amino acids while taking into consideration a set of metadata features and a context vector.

13. The system of claim 11, wherein the identifying further comprises:

matching one or more portions of the complete sequence of amino acids to one or more corresponding portions of a known peptide sequence;

determining a probability that the match between the one or more portions of the complete sequence of amino acids and the one or more corresponding portions of the known peptide sequence is indicative of a presence of the known peptide sequence in the sample; and when the probability is greater than a predetermined threshold, obtaining an identifier of the corresponding peptide or protein sequence from the reference proteome, wherein the unknown peptide or protein is identified based on the identifier.

14. The system of claim 11, wherein each long short term memory cell comprises three gates and a cell unit, wherein each of the three gates is configured to use a sigmoid activation, and wherein a cell state is determined by transforming data associated with at least one gate using a hyperbolic tangent function.

15. The system of claim 11, wherein each of the first and the second bidirectional recurrent neural network comprises at least two sets of hidden layers, wherein each set of the hidden layers is configured to processing data in a different direction.

* * * * *